US011259776B2

(12) United States Patent
Tsuruta

(10) Patent No.: US 11,259,776 B2
(45) Date of Patent: Mar. 1, 2022

(54) ULTRASOUND ENDOSCOPE WITH ULTRASOUND TRANSDUCER AND BALLOON INCLUDING A NOTCH PROVIDED ON OUTER CIRCUMFERENCE OF DISTAL WALL

(71) Applicant: OLYMPUS CORPORATION, Tokyo (JP)

(72) Inventor: Teppei Tsuruta, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 369 days.

(21) Appl. No.: 16/117,056

(22) Filed: Aug. 30, 2018

(65) Prior Publication Data
US 2019/0125305 A1     May 2, 2019

Related U.S. Application Data

(63) Continuation of application No. PCT/JP2016/078312, filed on Sep. 26, 2016.

(30) Foreign Application Priority Data

Mar. 3, 2016 (JP) .............................. JP2016-040958

(51) Int. Cl.
*A61B 8/00*     (2006.01)
*A61B 8/12*     (2006.01)
(Continued)

(52) U.S. Cl.
CPC ........ *A61B 8/4461* (2013.01); *A61B 1/00082* (2013.01); *A61B 8/12* (2013.01);
(Continued)

(58) Field of Classification Search
CPC ... A61B 8/4461; A61B 1/00082; A61B 8/445; A61B 8/12; A61B 1/0661; A61B 8/4488;
(Continued)

(56) References Cited

U.S. PATENT DOCUMENTS 7,692,364 B2    4/2010   Sawada et al.
8,134,280 B2    3/2012   Sawada et al.
(Continued)

FOREIGN PATENT DOCUMENTS

CN     104640507 A    5/2015
JP     H06-009608 U    2/1994
(Continued)

OTHER PUBLICATIONS

Harris, Kassem & Dhillon, Samjot. (2015). Enhancing Endobronchial Ultrasound Images Using a Water-based Lubricant Technique. Annals of the American Thoracic Society. vol. 12. No. 11. 1734-1736. 10.1513/AnnalsATS.201505-296LE. (Year: 2015).*
(Continued)

*Primary Examiner* — Serkan Akar
*Assistant Examiner* — Richmond J Van Winter
(74) *Attorney, Agent, or Firm* — Scully, Scott, Murphy & Presser, P.C.

(57) ABSTRACT

An ultrasound endoscope includes: an ultrasound transducer; a balloon groove in which a balloon band is fitted; a contact portion that constitutes a bottom surface of the balloon groove; a first wall portion that constitutes a proximal end side of the balloon groove and in which a first distance that is a distance from a center of a cross section orthogonal to an extension direction of the insertion portion to an outer circumference of the first wall portion is larger than a second distance that is a distance from the center of the cross section to the bottom surface; and a second wall portion that constitutes a distal end side of the balloon groove, in which a distance from the center of the cross section to an outer circumference of the second wall portion is larger than the second distance, and that includes a notch portion.

18 Claims, 6 Drawing Sheets

(51) Int. Cl.
   *A61B 1/00* (2006.01)
   *A61B 1/06* (2006.01)
(52) U.S. Cl.
   CPC ............ *A61B 8/445* (2013.01); *A61B 8/4455* (2013.01); *A61B 1/0661* (2013.01); *A61B 8/4488* (2013.01)
(58) Field of Classification Search
   CPC .. A61B 1/00101; A61B 8/4281; A61B 8/4455
   See application file for complete search history.

(56) References Cited

U.S. PATENT DOCUMENTS

| | | | |
|---|---|---|---|
| 2009/0275839 A1 | 11/2009 | Sawada et al. | |
| 2011/0218443 A1 | 9/2011 | Sawada et al. | |
| 2013/0137990 A1* | 5/2013 | Tsuruta | A61B 1/00087 600/466 |
| 2015/0173590 A1* | 6/2015 | Fujimura | A61B 8/445 600/466 |

FOREIGN PATENT DOCUMENTS

| | | |
|---|---|---|
| JP | 2001-112756 A | 4/2001 |
| JP | 2003-265482 A | 9/2003 |
| JP | 2006-204642 A | 8/2006 |
| JP | 2008-099745 A | 5/2008 |
| WO | WO-2013084555 A1 * 6/2013 | ......... A61B 1/00082 |

OTHER PUBLICATIONS

Extended Supplementary European Search Report dated Oct. 29, 2019 in European Patent Application No. 16 89 2652.5.
International Search Report dated Nov. 1, 2016 issued in PCT/JP2016/078312.
Chinese Office Action dated Jun. 18, 2020 in Chinese Patent Application No. 201680083107.4, together with an English language translation.

* cited by examiner

ULTRASOUND ENDOSCOPE WITH ULTRASOUND TRANSDUCER AND BALLOON INCLUDING A NOTCH PROVIDED ON OUTER CIRCUMFERENCE OF DISTAL WALL

CROSS-REFERENCE TO RELATED APPLICATIONS

This application is a continuation of PCT international application Ser. No. PCT/JP2016/078312 filed on Sep. 26, 2016 which designates the United States, incorporated herein by reference, and which claims the benefit of priority from Japanese Patent Application No. 2016-040958, filed on Mar. 3, 2016, incorporated herein by reference.

BACKGROUND

1. Technical Field

The present disclosure relates to an ultrasound endoscope.

2. Related Art

In the related art, there is a known method of performing observation, in an ultrasound endoscope having an ultrasound transducer at its distal end, by injecting deaerated water into a balloon that is disposed so as to cover an outer circumference of the ultrasound transducer and by bringing the balloon into close contact with an observed region, such as an alimentary canal (for example, see Japanese Laid-open Patent Publication No. 2006-204642). In the ultrasound endoscope, balloon bands provided at both ends of the balloon are fitted into balloon grooves provided at the distal end of the ultrasound endoscope.

With the ultrasound endoscope that performs observation by using such a balloon, the balloon needs to be removed from the ultrasound endoscope after the observation.

SUMMARY

In some embodiments, an ultrasound endoscope includes: an ultrasound transducer, with a radial type, that is provided at a distal end of an insertion portion configured to be inserted into a subject, the ultrasound transducer being configured to send ultrasound into the subject and receive the ultrasound reflected in the subject; a balloon groove that is provided on a distal end side of the ultrasound transducer and in which a balloon band is fitted, the balloon band being provided at an end portion of a balloon that is attached to cover an outer surface of the ultrasound transducer; a contact portion that constitutes a bottom surface of the balloon groove and that is in contact with the balloon band; a first wall portion that constitutes a proximal end side of the balloon groove and in which a first distance that is a distance from a center of a cross section orthogonal to an extension direction of the insertion portion to an outer circumference of the first wall portion is larger than a second distance that is a distance from the center of the cross section to the bottom surface; and a second wall portion that constitutes a distal end side of the balloon groove, in which a third distance that is a distance from the center of the cross section to an outer circumference of the second wall portion is larger than the second distance, and that includes a notch portion provided with a surface in which a distance from the center of the cross section to the surface of the notch portion is smaller than the sum of the second distance and a thickness of the balloon band, the notch portion being configured to visually recognize the balloon band fitted into the balloon groove when the distal end of the insertion portion is viewed from the distal end side of the insertion portion.

In some embodiments, an ultrasonic endoscope includes: an ultrasound transducer, with a radial type, that is provided at a distal end of an insertion portion configured to be inserted into a subject, the ultrasound transducer being configured to send ultrasound into the subject and receive the ultrasound reflected in the subject; and a balloon groove that is provided on a distal end side of the ultrasound transducer and in which a balloon band is fitted, the balloon band being provided at an end portion of a balloon that is attached to cover an outer surface of the ultrasound transducer. The balloon groove includes a contact portion that constitutes a bottom surface of the balloon groove and that is in contact with the balloon band, a first wall portion that constitutes a wall surface of a proximal end side of the balloon groove, and a second wall portion that constitutes a wall surface of a distal end side of the balloon groove and that includes a notch portion provided with a surface in D-cut shape formed on a part of the second wall portion, the notch portion being configured to visually recognize the balloon band fitted into the balloon groove when the distal end of the insertion portion is viewed from the distal end side of the insertion portion, and when a tool for removing the balloon band is inserted along the surface, the contact portion is prevented from being damaged caused by a distal end of the tool being brought into contact with the contact portion.

In some embodiments, an ultrasonic endoscope includes: an ultrasound transducer that is provided at a distal end of an insertion portion configured to be inserted into a subject, the ultrasound transducer being configured to send ultrasound into the subject and receive the ultrasound reflected in the subject; a second balloon groove that is provided on a proximal end side of the ultrasound transducer and in which a balloon band is fitted, the balloon band being provided at an end portion of a balloon that is attached to cover an outer surface of the ultrasound transducer; a second contact portion that constitutes a bottom surface of the second balloon groove and that is in contact with the balloon band; a third wall portion that constitutes a proximal end side of the second balloon groove and in which a fifth distance that is a distance from a center of a cross section orthogonal to an extension direction of the insertion portion to an outer circumference of the third wall portion is larger than a fourth distance that is a distance from the center of the cross section to the bottom surface; and a fourth wall portion that constitutes a distal end side of the second balloon groove, in which a sixth distance that is a distance from the center of the cross section to an outer circumference of the fourth wall portion is larger than the fourth distance, and that includes a notch portion provided with a surface in which a distance from the center of the cross section to the surface of the notch portion is smaller than the sum of the fourth distance and a thickness of the balloon band.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
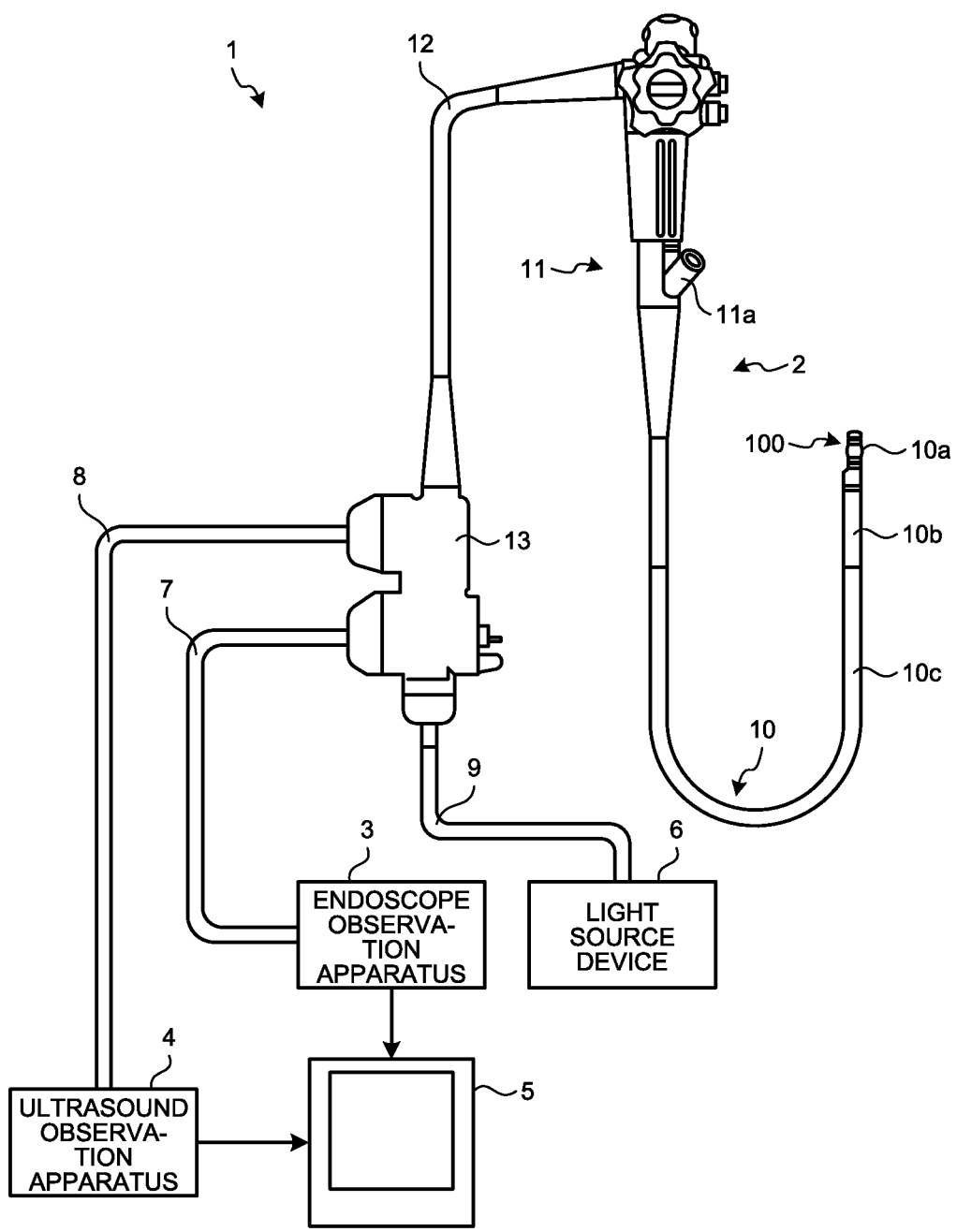
FIG. 1 is a schematic view illustrating an ultrasound endoscope system that includes an ultrasound endoscope according to an embodiment of the disclosure.

Preferred embodiments of an ultrasound endoscope according to the disclosure will be explained with reference to accompanying drawings. Furthermore, the disclosure is not limited to the embodiments. In the embodiments described below, an ultrasound endoscope in which a balloon groove is formed on both the proximal end side and the distal end side of an ultrasound transducer is described as an example; however, the ultrasound endoscope according to the disclosure can be applied to a typically used ultrasound endoscope in which a balloon groove is formed and also applied to an ultrasound endoscope in which, for example, a balloon groove is formed only on the proximal end side of an ultrasound transducer.

In the drawings, components that are identical to those in embodiments are assigned the same reference numerals. The drawings used for the descriptions below are only schematic illustrations. The relationship between the thickness and the width of each member, the proportions of each member, and so on are different from those used in practice. The size or reduction in scale of elements may sometimes differ between the drawings.

EMBODIMENT

FIG. 1 is a schematic view illustrating an ultrasound endoscope system that includes an ultrasound endoscope according to an embodiment of the disclosure. An ultrasound endoscope system 1 illustrated in FIG. 1 includes an ultrasound endoscope 2, an endoscope observation apparatus 3, an ultrasound observation apparatus 4, a display device 5, a light source device 6, a video cable 7 that connects the ultrasound endoscope 2 and the endoscope observation apparatus 3, an ultrasound cable 8 that connects the ultrasound endoscope 2 and the ultrasound observation apparatus 4, and a light source cable 9 that connects the ultrasound endoscope 2 and the light source device 6.

The ultrasound endoscope 2 is formed by combining an endoscope observation unit, which has observation optical system constituted by lenses or the like and has an image sensor, and an ultrasound transducer and has an endoscope observation function and an ultrasound measurement function. The endoscope observation apparatus 3 controls the endoscope observation function and processes an output signal that is output from the ultrasound endoscope 2 obtained from endoscope observation. The ultrasound observation apparatus 4 controls the ultrasound measurement function and processes an output signal that is output from the ultrasound endoscope 2 obtained from ultrasound measurement. The display device 5 acquires signals output from, for example, the endoscope observation apparatus 3 and the ultrasound observation apparatus 4 and appropriately displays at least one of an endoscope image and an ultrasound tomogram. The light source device 6 includes a light source for supplying illumination light that is used to perform endoscope observation.

The ultrasound endoscope 2 includes an insertion portion 10 that is inserted into the body, that sends an ultrasound signal into the subject, and that receives the ultrasound signal reflected in the subject; an operating unit 11 that is consecutively provided on the proximal end side of the insertion portion 10; and an universal cable 12 extended from a side portion of the operating unit 11. The universal cable 12 includes a connector portion 13 that is provided on the end portion located on the different side from the operating unit 11 side and that is connected to each of the video cable 7, the ultrasound cable 8, and the light source cable 9.

The insertion portion 10 is formed by consecutively connecting, in the order from the distal end side, a distal end portion 10a that is provided with an ultrasound transducer 100, which will be described later; a bending portion 10b that is formed so as to be freely bendable; and a flexible tube portion 10c that has flexibility. The proximal end of the flexible tube portion 10c is consecutively connected on the distal end side of the operating unit 11. Furthermore, in the present specification, the distal end side along the direction in which the insertion portion 10 is inserted (an upper part along the plane of the drawing in FIG. 1) is referred to as a distal end side and the proximal end side along the direction in which the insertion portion 10 is inserted (a lower part along the plane of the drawing in FIG. 1) is referred to as a proximal end side.

A treatment instrument insertion port 11a that is used to introduce a puncture needle or the like that is a treatment instrument is provided in the operating unit 11. A treatment instrument insertion path is provided inside the insertion portion 10 and the treatment instrument insertion port 11a functions as an insertion port of the treatment instrument insertion path.

Both the ultrasound endoscope 2 and the endoscope observation apparatus 3 are electrically connected by the video cable 7 that is connected to the connector portion 13. Both the ultrasound endoscope 2 and an ultrasound observation apparatus 4 are electrically connected by the ultrasound cable 8 that is connected to the connector portion 13. The light source cable 9 is an optical fiber cable and both the ultrasound endoscope 2 and the light source device 6 introduce, to the ultrasound endoscope 2, illumination light emitted from a light source of the light source device 6 by the light source cable 9 that is connected to the connector portion 13.

Figure 2:
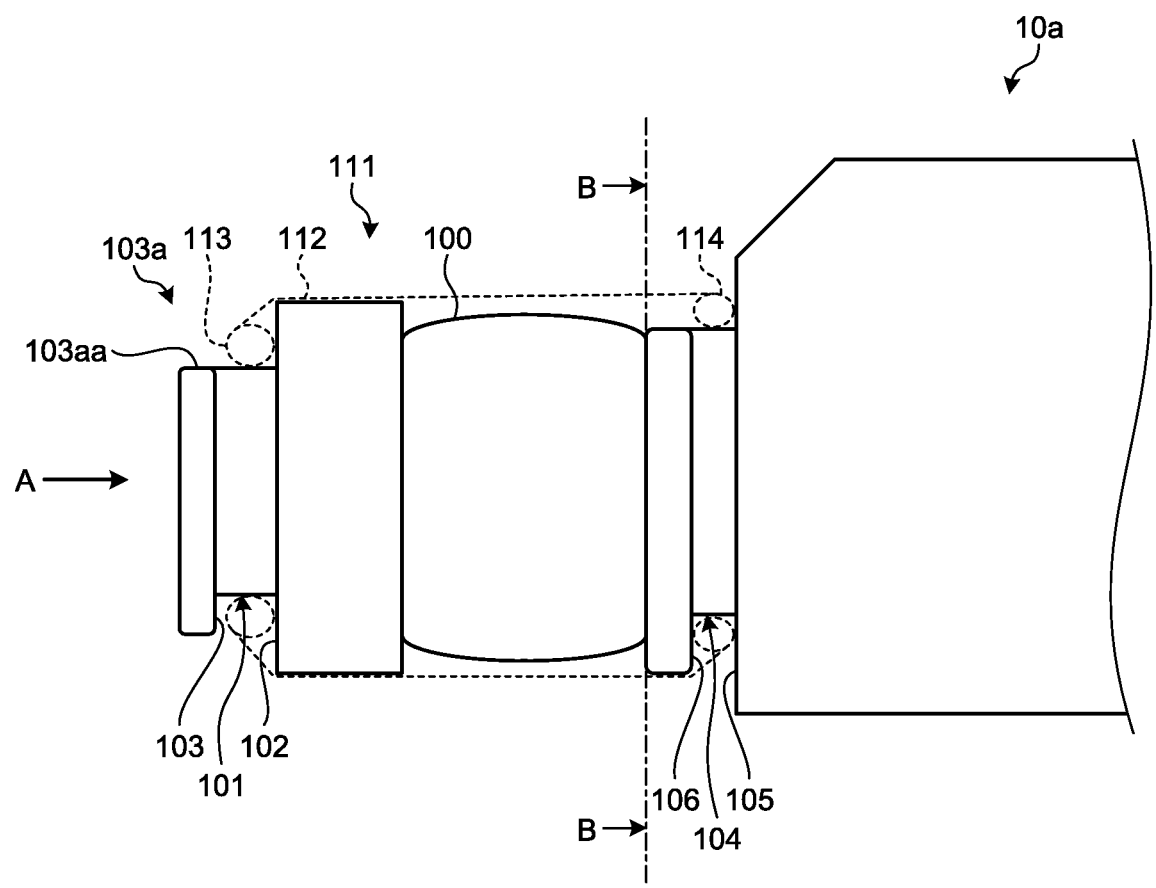
FIG. 2 is a side view illustrating the configuration of a distal end portion of an insertion portion of the ultrasound endoscope illustrated in FIG. 1.
Figure 3:
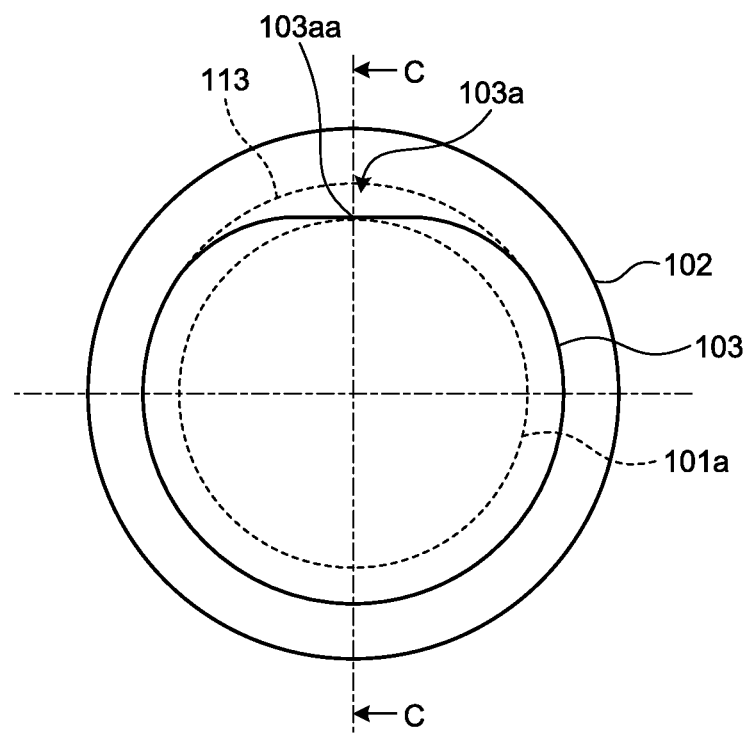
FIG. 3 is a diagram as viewed from an arrow A illustrated in FIG. 2.
Figure 4:
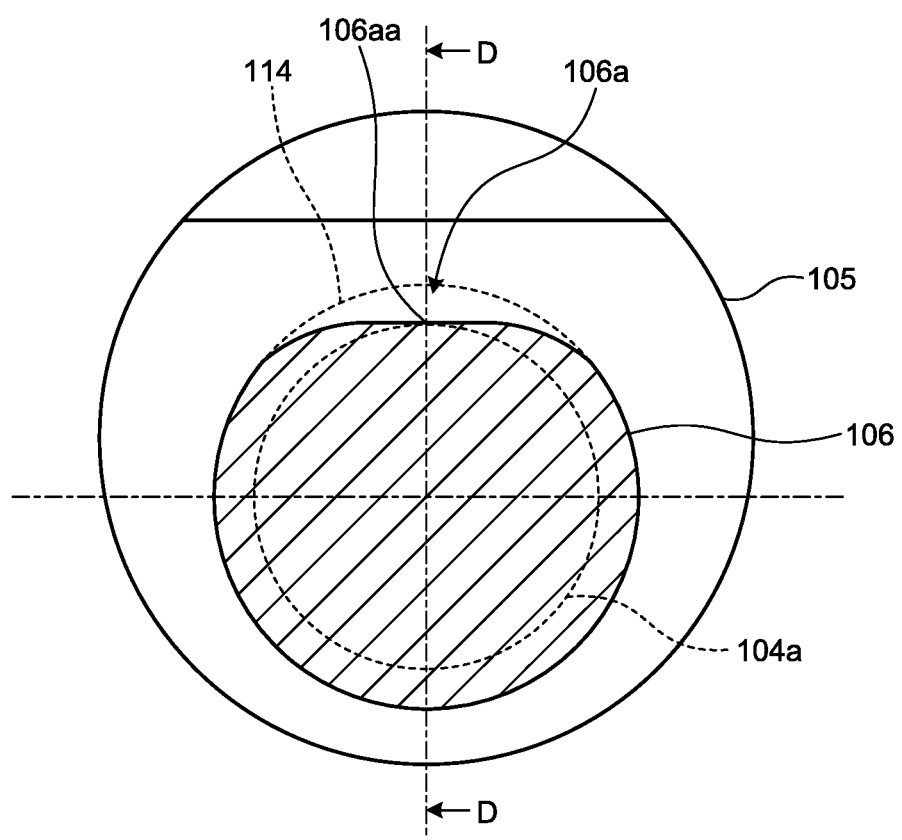
FIG. 4 is a cross sectional view associated with a line B-B illustrated in FIG. 2.

FIG. 2 is a side view illustrating the configuration of the distal end portion of the insertion portion of the ultrasound endoscope illustrated in FIG. 1. FIG. 3 is a diagram as viewed from an arrow A illustrated in FIG. 2. FIG. 4 is a cross sectional view associated with a line B-B illustrated in FIG. 2. Furthermore, FIG. 2 illustrates a cross section associated with the cross sectional view of a balloon 111 taken along a line C-C illustrated in FIG. 3 in the state in which the balloon 111 is attached to the distal end portion 10a of the insertion portion 10 so as to cover the outer surface of the ultrasound transducer 100 (cross sectional view taken along a line D-D illustrated in FIG. 4).

As illustrated in FIG. 2, the ultrasound transducer 100 is provided at the distal end portion 10a that is located at the distal end of the insertion portion 10 to be inserted into the subject. A distal-end-side balloon groove 101 that is a balloon groove is provided on the distal end side of the ultrasound transducer 100. The proximal end side of the distal-end-side balloon groove 101 is constituted by a first wall surface that is a surface of a first wall portion 102 on the distal end side. The distal end side of the distal-end-side balloon groove 101 is constituted by the second wall surface that is a surface of a second wall portion 103 on the proximal end side. Furthermore, a proximal-end-side balloon groove 104 that is a balloon groove is provided on the proximal end side of the ultrasound transducer 100. The proximal end side of the proximal-end-side balloon groove 104 is constituted by the first wall surface that is a surface of a first wall portion 105 on the distal end side. The distal end side of the proximal-end-side balloon groove 104 is constituted by the second wall surface that is a surface of a second wall portion 106 on the proximal end side.

The balloon 111 includes a main body 112 that covers the outer surface of the ultrasound transducer 100, a distal-end-side balloon band 113 that is provided on the distal end side of the main body 112, and a proximal-end-side balloon band 114 that is provided on the proximal end side of the main body 112. Then, the distal-end-side balloon band 113 is fitted into the distal-end-side balloon groove 101, whereas the proximal-end-side balloon band 114 is fitted into the proximal-end-side balloon groove 104.

The ultrasound transducer 100 sends ultrasound into the subject and receives ultrasound (ultrasound echo) reflected in the subject. The outer circumference of the ultrasound transducer 100 is covered by the acoustic lens. The acoustic lens has a convex shape or a concave shape on one of the surfaces and has a function of diffusing ultrasound when externally emitting the ultrasound received from the ultrasound transducer 100 and extracting the ultrasound when acquiring the ultrasound received from outside into the ultrasound transducer 100.

As illustrated in FIG. 3, a contact portion 101a that constitutes the bottom surface of the distal-end-side balloon groove 101 and that is in contact with the distal-end-side balloon band 113 fitted into the distal-end-side balloon groove 101 has a circular shape. Furthermore, in the present specification, each of the directions from the center of the distal-end-side balloon groove 101 having a circular shape toward the outer side along the cross section orthogonal to the extension direction of the insertion portion 10 is referred to as a radial direction. Furthermore, the distance from the center to the outer circumference in each of the radial directions is referred to as a radius.

In each of the radial directions, a radius (a first distance) of a first wall surface of the first wall portion 102 is larger than a radius (a second distance) of the contact portion 101a of the distal-end-side balloon groove 101. Namely, the outer circumference of the first wall portion 102 has the same center as the contact portion 101a of the distal-end-side balloon groove 101 and has a circular shape with a larger radius than the contact portion 101a.

The second wall portion 103 has, in each of the radial directions, a wall surface in which a radius (a third distance) of the second wall surface of the second wall portion 103 is larger than the radius (the second distance) of the contact portion 101a of the distal-end-side balloon groove 101. Furthermore, the second wall portion 103 has a notch portion 103a in a D-cut shape, the notch portion 103a being provided with a surface 103aa in which the radius (the third distance) of a one direction (upward along the plane of the drawing in FIG. 3) from among the radial directions is reduced. The radius (the third distance) of the surface 103aa of the notch portion 103a is equal to or greater than the radius of the contact portion 101a and is smaller than the radius of the second wall portion 103 in the direction in which the radius of the second wall portion 103 is the largest.

As illustrated in FIG. 4, a contact portion 104a that constitutes the bottom surface of the proximal-end-side balloon groove 104 and that is in contact with the proximal-end-side balloon band 114 fitted into the proximal-end-side balloon groove 104 has a circular shape.

In each of the radial directions, the radius (the first distance) of the first wall surface of the first wall portion 105 is larger than the radius of the contact portion 104a of the proximal-end-side balloon groove 104. Namely, outer circumference of the first wall portion 105 has the same center as the contact portion 104a of the proximal-end-side balloon groove 104 and has a circular shape with a larger radius than the contact portion 104a.

The second wall portion 106 has, in each of the radial directions, a wall surface in which the radius (the third distance) of the second wall surface of the second wall portion 106 is larger than the radius (the second distance) of the contact portion 104a of the proximal-end-side balloon groove 104. Furthermore, the second wall portion 106 has a notch portion 106a in a D-cut shape, the notch portion 106a having a surface 106aa in which the radius (the third distance) of a one direction (upward along the plane of the drawing in FIG. 4) from among the radial directions is reduced. The radius (the third distance) of the surface 106aa of the notch portion 106a is equal to or greater than the radius of the contact portion 104a and is smaller than the radius of the second wall portion 106 in the direction in which the radius of the second wall portion 106 is the largest.

In the following, an operation performed when the balloon 111 is removed from the ultrasound endoscope 2 will be described. First, a user inflates the main body 112 of the balloon 111 by introducing a small amount of liquid, such as water, into the balloon 111. In this state, the user holds the main body 112 of the balloon 111 by the user's fingers and removes the proximal-end-side balloon band 114 that is fitted into the proximal-end-side balloon groove 104. Furthermore, the user pulls the held balloon 111 toward the distal end side and removes the distal-end-side balloon band 113 that is fitted into the distal-end-side balloon groove 101. At this time, in some cases, the balloon 111 is broken and the distal-end-side balloon band 113 is left in the distal-end-side balloon groove 101.

Here, in the ultrasound endoscope 2, it is possible to remove the distal-end-side balloon band 113 from the distal-end-side balloon groove 101 by using a tool with a sharp distal end, such as a toothpick. The user inserts the tool with the sharp distal end from the distal end side illustrated in FIG. 2 along the surface 103aa of the notch portion 103a of the second wall portion 103. Then, the distal end of the tool with the sharp distal end abuts against the surface of the first wall portion 102 on the distal end side. Subsequently, the user lifts the tool with the sharp distal end in a direction in which the tool with the sharp distal end away from the contact portion 101a of the distal-end-side balloon groove 101 (upward along the plane of the drawing in FIG. 2). Then, the user further pulls the tool with the sharp distal end toward for example, the distal end side in a state in which the distal-end-side balloon band 113 is caught by the tool with the sharp distal end and then removes the distal-end-side balloon band 113 from the distal-end-side balloon groove 101. Alternatively, the user can remove the distal-end-side balloon band 113 by the user's fingers from the state in which the distal-end-side balloon band 113 is caught by the tool with the sharp distal end or can cut the distal-end-side balloon band 113 by a pair of scissors, a scalpel, or the like.

As described above, because the notch portion 103a is formed on the second wall portion 103, the tool with the sharp distal end is easily inserted between the distal-end-side balloon band 113 and the distal-end-side balloon groove 101; therefore, the ultrasound endoscope 2 is an ultrasound endoscope in which a balloon is easily removed.

Furthermore, with the ultrasound endoscope 2, because the tool with the sharp distal end is inserted along the surface 103aa of the notch portion 103a of the second wall portion 103, the distal end of the tool with the sharp distal end is prevented from being damaged caused by being brought into contact with the contact portion 101a of the distal-end-side balloon groove 101. If the contact portion 101a of the distal-end-side balloon groove 101 is damaged, leakage may sometimes occur when liquid, such as water, is introduced into the balloon 111 attached to the ultrasound endoscope 2.

Furthermore, in the ultrasound endoscope 2, it is preferable that a radius of a portion of the first wall portion 102 across the distal-end-side balloon groove 101 from the notch portion 103a is larger than the radius of the notch portion 103a. In this case, the distal end of the tool with the sharp distal end that was inserted along the surface 103aa of the notch portion 103a of the second wall portion 103 abuts against the surface of the distal end side of the first wall portion 102. Consequently, the tool with the sharp distal end is prevented from being damaged caused by being brought into contact with the acoustic lens that covers the ultrasound transducer 100.

Furthermore, when the balloon 111 is removed from the ultrasound endoscope 2, the proximal-end-side balloon band 114 fitted into the proximal-end-side balloon groove 104 is sometimes left in the proximal-end-side balloon groove 104. Because the notch portion 106a is also formed on the second wall portion 106, the tool with the sharp distal end is easily inserted between the proximal-end-side balloon band 114 and the proximal-end-side balloon groove 104, the ultrasound endoscope 2 is an ultrasound endoscope in which the balloon is also easily removed on the proximal end side.

Furthermore, in the ultrasound endoscope 2, it is preferable to visually recognize the distal-end-side balloon band 113 fitted into the distal-end-side balloon groove 101 when viewing the distal end of the insertion portion 10 from the distal end side (direction of the arrow A illustrated in FIG. 2) of the extension direction of the insertion portion 10. If the distal-end-side balloon band 113 can be visually recognized, the tool with the sharp distal end can be easily inserted between the distal-end-side balloon band 113 and the distal-end-side balloon groove 101. Thus, it is preferable that the radius of the surface 103aa of the notch portion 103a be smaller than the sum of the radius of the contact portion 101a and the thickness of the distal-end-side balloon band 113.

Figure 5:
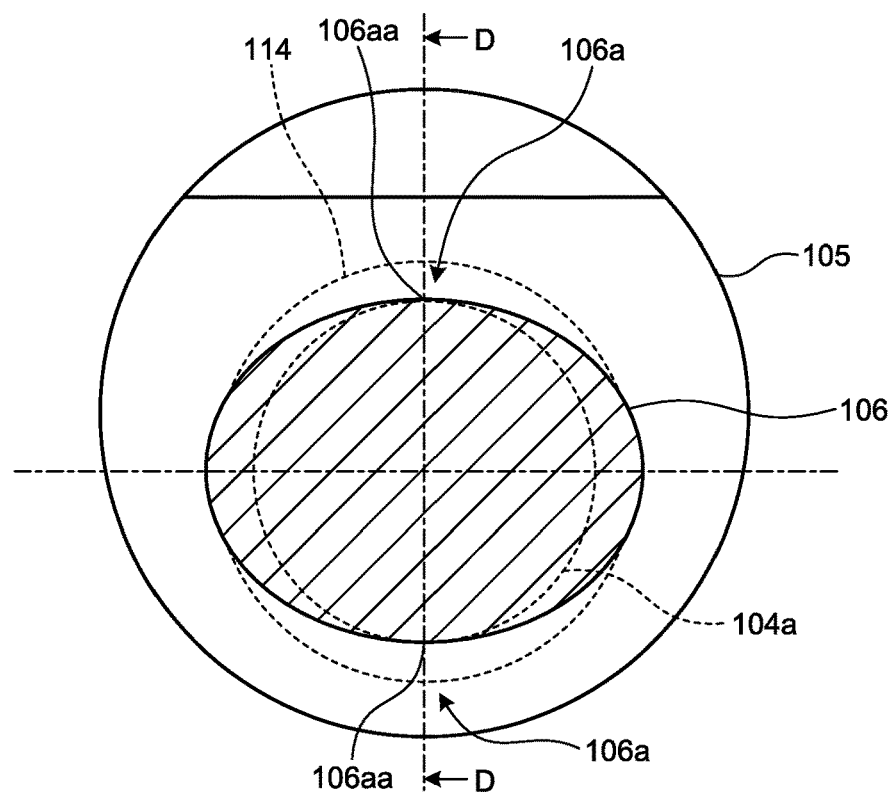
FIG. 5 is a cross sectional view illustrating another example associated with the line B-B illustrated in FIG. 2.

Furthermore, in the ultrasound endoscope 2, the second wall portion 103 and the second wall portion 106 have the notch portion 103a and the notch portion 106a, respectively, in a one direction from among the radial directions; however, notch portions may also be included in a plurality of directions in the radial directions. FIG. 5 is a cross sectional view illustrating another example associated with the line B-B illustrated in FIG. 2. As illustrated in FIG. 5, the second wall portion 106 has an oval shape in cross section and has two notch portions 106a having surfaces 106aa in which radii (the third distance) of two directions (upward and downward along the plane of the drawing in FIG. 5) from among the radial directions are reduced.

Furthermore, in the ultrasound endoscope 2, the surface 103aa of the notch portion 103a of the second wall portion 103 may also be reinforced because the surface 103aa is brought into contact with the tool with the sharp distal end. Furthermore, because the surface 103aa of the notch portion 103a of the second wall portion 103 and the tool with the sharp distal end slide each other, it is preferable to use a material having an excellent sliding property. In order to implement this, the surface 103aa of the notch portion 103a of the second wall portion 103 may also be coated by, for example, Teflon (registered trademark), fluorine, diamond, or the like. Furthermore, the surface 103aa of the notch portion 103a of the second wall portion 103 may also be formed of a material, such as hard titanium.

First Modification

Figure 6:
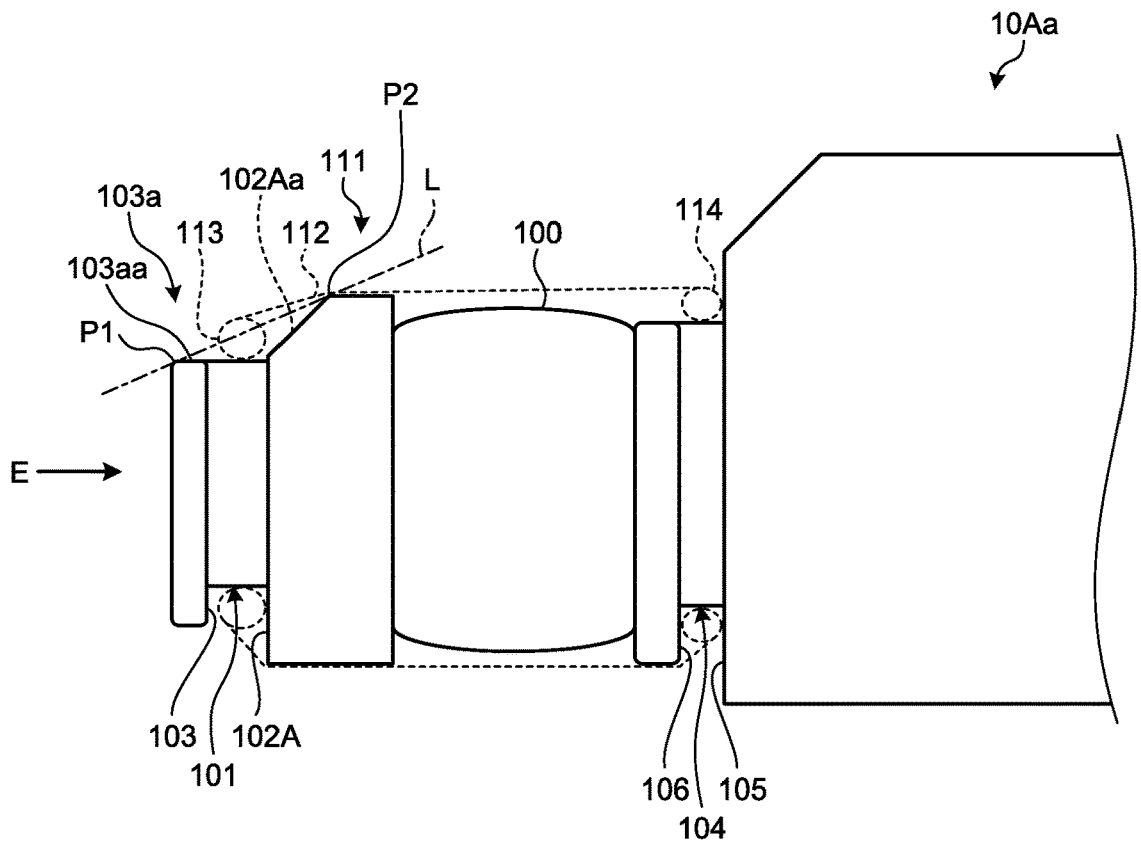
FIG. 6 is a side view illustrating the configuration of a distal end portion of an insertion portion of an ultrasound endoscope according to a first modification of the embodiment.
Figure 7:
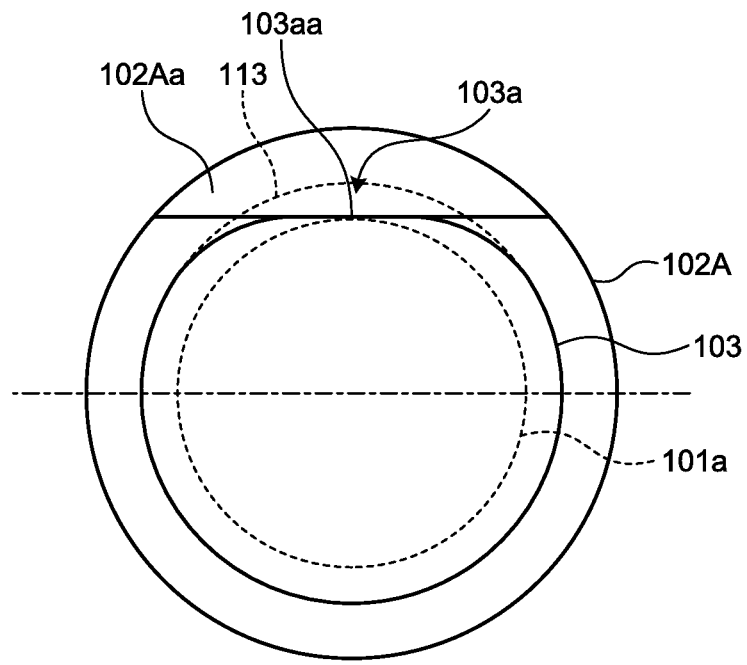
FIG. 7 is a diagram as viewed from an arrow E illustrated in FIG. 6.

FIG. 6 is a side view illustrating the configuration of a distal end portion of an insertion portion of an ultrasound endoscope according to a first modification of the embodiment. FIG. 7 is a diagram as viewed from an arrow E illustrated in FIG. 6. The configuration of a distal end portion 10Aa of an ultrasound endoscope according to a first modification will be described with reference to FIG. 6 and FIG. 7.

As illustrated in FIG. 7, in each of the radial directions, a radius (the first distance) of a first wall surface of a first wall portion 102A that constitutes the proximal end side of the distal-end-side balloon groove 101 is larger than the radius (the second distance) of the contact portion 101a of the distal-end-side balloon groove 101. Namely, an outer circumference of the first wall portion 102A has the same center as the contact portion 101a of the distal-end-side balloon groove 101 and has a circular shape with a larger radius than the contact portion 101a. Furthermore, an inclined surface 102Aa in which a radius (the first distance) is decreased toward the distal end side along the extension direction of the insertion portion 10 is formed on the first wall portion 102A facing the notch portion 103a in the radial direction of the first wall portion 102A.

In the ultrasound endoscope according to the first modification, the distal end of the tool with the sharp distal end that is inserted along the surface 103aa of the notch portion 103a of the second wall portion 103 moves forward along the inclined surface 102Aa of the first wall portion 102A. Consequently, the tool with the sharp distal end is prevented from being damaged caused by being brought into contact with the acoustic lens that covers the ultrasound transducer 100. Furthermore, the inclined surface 102Aa may also be connected to the distal-end-side balloon groove 101 by a smoothly curved surface.

Furthermore, in the ultrasound endoscope according to the first modification, when removing the distal-end-side balloon band 113 that is left behind in the distal-end-side balloon groove 101, a user can remove the distal-end-side balloon band 113 from the distal-end-side balloon groove 101 without using any tool by sliding by using the user's fingers the distal-end-side balloon band 113 to the distal end side along the inclined surface 102Aa of the first wall portion 102A.

Furthermore, in the ultrasound endoscope according to the first modification, in the case where, in a straight line group where each straight line is obtained by connecting an arbitrary point (for example, a point P1 in FIG. 6) on a front surface of the surface 103aa of the notch portion 103a and an arbitrary point (for example, a point P2 in FIG. 6) on a front surface of the first wall portion 102A, each straight line (for example, a straight line L in FIG. 6) included in the straight line group is disposed so as not to intersect the first wall portion 102A and the second wall portion 103 except for the two points, it is preferable that a three-dimensionally spreading area through which the straight line group passes does not intersect the acoustic lens that covers the ultrasound transducer 100. The reason for this is to prevent the tool with the sharp distal end that has moved forward along the inclined surface 102Aa of the first wall portion 102A from being damaged caused by being brought into contact with the acoustic lens that covers the ultrasound transducer 100.

Second Modification

Figure 8:
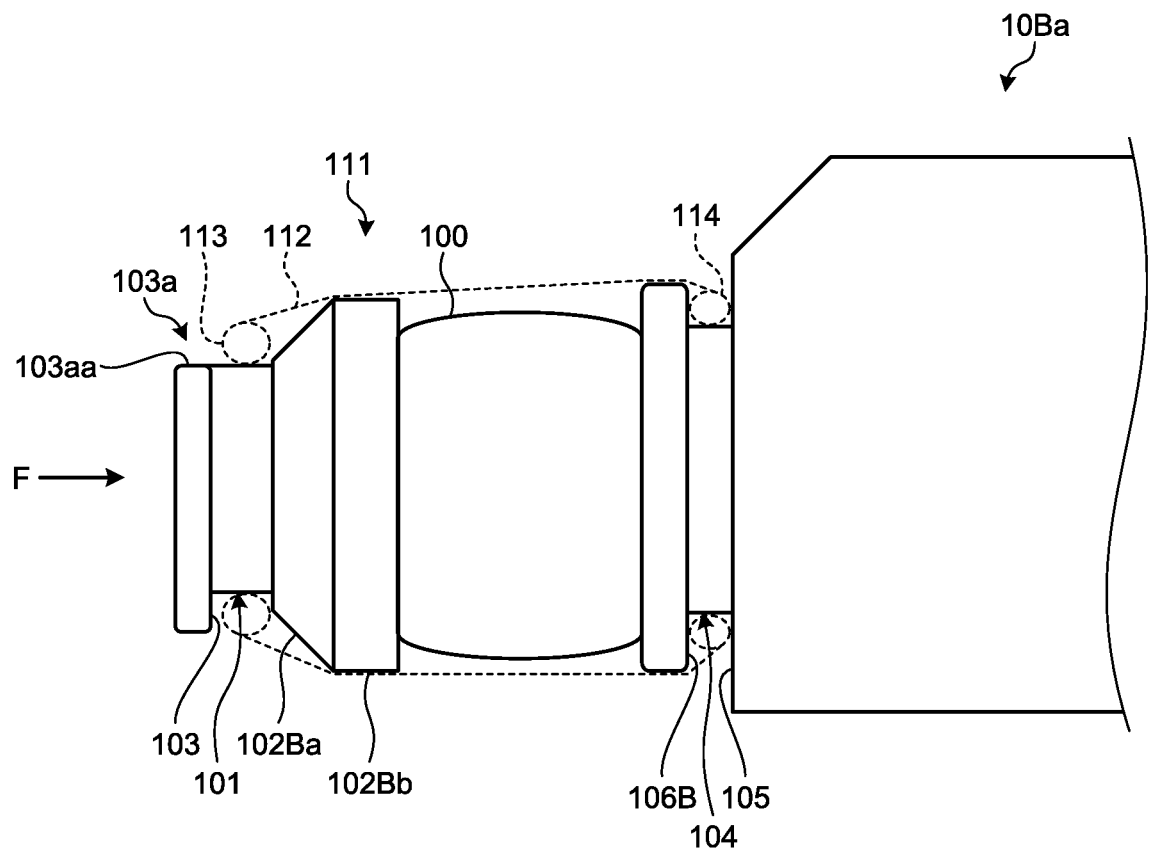
FIG. 8 is a side view illustrating the configuration of a distal end portion of an insertion portion of an ultrasound endoscope according to a second modification of the embodiment.
Figure 9:
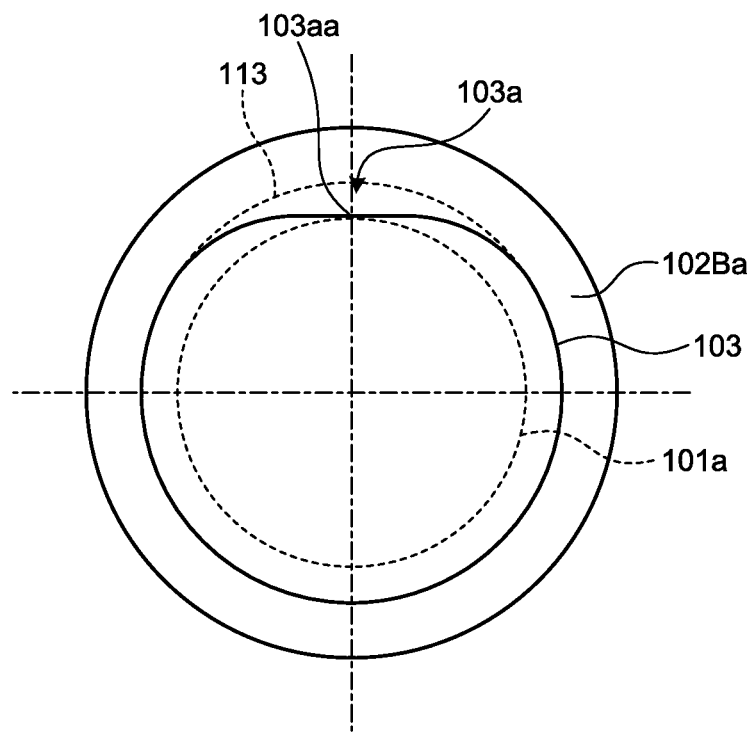
FIG. 9 is a diagram as viewed from an arrow F illustrated in FIG. 8.

FIG. 8 is a side view illustrating the configuration of a distal end portion of an insertion portion of an ultrasound endoscope according to a second modification of the embodiment. FIG. 9 is a diagram as viewed from an arrow F illustrated in FIG. 8. The configuration of a distal end portion 10Ba of the ultrasound endoscope according to the second modification will be described with reference to FIG. 8 and FIG. 9.

As illustrated in FIG. 9, in each of the radial directions, a radius (the first distance) of a first wall surface of a first wall portion 102B that constitutes the proximal end side of the distal-end-side balloon groove 101 is larger than the radius (the second distance) of the contact portion 101a of the distal-end-side balloon groove 101. Namely, an outer circumference of the first wall portion 102B has the same center as the contact portion 101a of the distal-end-side balloon groove 101 and has a circular shape with a larger radius than the contact portion 101a. Furthermore, an inclined surface 102Ba in which a radius (the first distance) is decreased toward the distal end side along the extension direction of the insertion portion 10 is formed on the first wall portion 102B facing the notch portion 103a in the radial direction of the first wall portion 102B. The inclined surface 102Ba is formed around the entire circumference of the first wall portion 102B. The inclined surface 102Ba is connected to a cylindrical portion 102Bb having a constant radius along the extension direction of the insertion portion 10.

In the ultrasound endoscope according to the second modification, the distal end of the tool with the sharp distal end inserted along the surface 103aa of the notch portion 103a of the second wall portion 103 moves ahead along the inclined surface 102Ba of the first wall portion 102B. Consequently, the tool with the sharp distal end is prevented from being damaged caused by being brought into contact with the acoustic lens that covers the ultrasound transducer 100. In this way, the inclined surface 102Ba may also be formed around the entire circumference of the radial direction.

Furthermore, in the ultrasound endoscope according to the second modification, a notch portion is not formed on a second wall portion 106B of the distal end side of the proximal-end-side balloon groove 104. In this way, a notch portion may also be disposed on one side of the distal end side and proximal end side of the ultrasound transducer 100.

Figure 10:
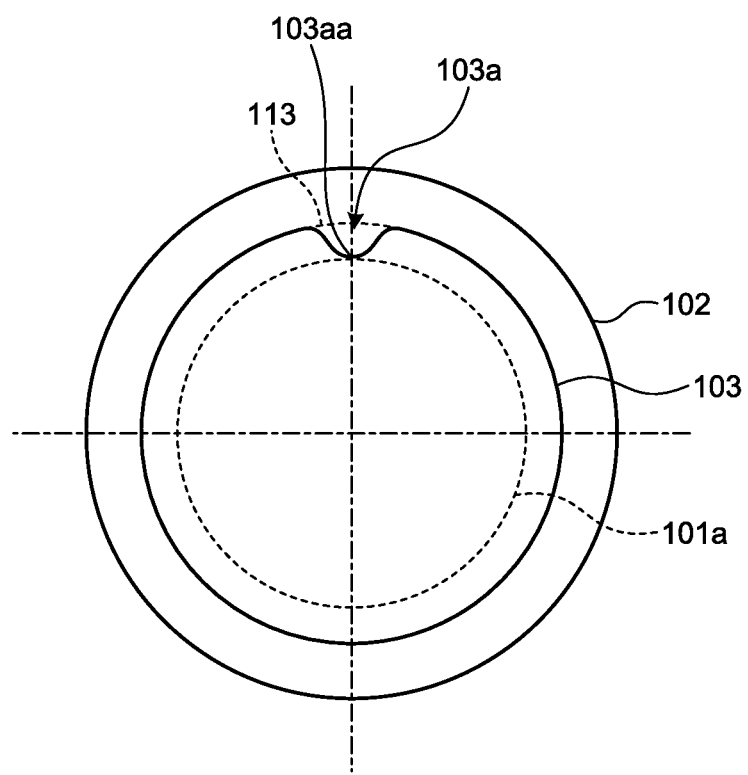
FIG. 10 is a diagram illustrating the configuration of a distal end portion of an insertion portion according to another modification of the embodiment.

FIG. 10 is a diagram illustrating the configuration of a distal end portion of an insertion portion according to another modification of the embodiment. FIG. 10 is a diagram of the ultrasound endoscope associated with FIG. 3 viewed from the distal end side. As illustrated in FIG. 10, the notch portion 103a is not limited to the D-cut shape, but may also be, for example, a concave portion. By forming the notch portion 103a as the concave portion illustrated in FIG. 10, a cutting instrument, such as a pair of scissors, is not able to enter the notch portion 103a. Consequently, the contact portion 101a of the distal-end-side balloon groove 101 is prevented from being damaged by such a cutting instrument.

Furthermore, in the embodiment described above, the ultrasound endoscope having a radial type ultrasound transducer has been described; however, the embodiment is not limited to this. For example, the embodiment can be applied to an ultrasound endoscope having a convex type ultrasound transducer.

Further advantages and modifications can be easily derived by those skilled in the art. Therefore, the disclosure in its broader aspect is not limited to the specific details and representative embodiments shown and described herein. Accordingly, various modifications may be made without departing from the spirit or scope of the general inventive concept as defined by the appended claims and their equivalents.

According to some embodiments, it is possible to implement an ultrasound endoscope in which a balloon is easily removed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope comprising:
   an ultrasound transducer provided at a distal end of an insertion portion configured to be inserted into a subject, the ultrasound transducer being configured to radially transmit ultrasound into the subject and receive the ultrasound reflected from the subject;
   a balloon groove provided on a distal end side of the ultrasound transducer, the balloon groove being configured to fit a balloon band, the balloon band being provided at an end portion of a balloon covering an outer surface of the ultrasound transducer; and
   a distal wall forming a distal end side of the balloon groove, the distal wall having a notch configured to visually recognize the balloon band fitted into the balloon groove when the distal end of the insertion portion is viewed from a distal end side of the insertion portion, wherein
   the notch is partially provided only on a portion of an outer circumference of the distal wall in a radial direction relative to an insertion axis extending through a center of a cross-section of the insertion portion,
   the notch defining a surface on the outer circumference of the distal wall having a first radial distance from the insertion axis to the surface, the first radial distance being equal to or larger than a second radial distance and smaller than a third radial distance,
   the second radial distance being from the insertion axis to a contact portion that forms a bottom surface of the balloon groove; and the third radial distance being a sum of the second radial distance and a thickness of the balloon band.

2. The ultrasound endoscope according to claim 1, wherein the notch is concave relative to the insertion axis.

3. The ultrasound endoscope according to claim 1, wherein the first radial distance is equal to the second radial distance.

4. The ultrasound endoscope according to claim 1, further comprising a coating applied to the notch, the coating having an improved sliding property relative to a sliding property of a material forming the notch.

5. The ultrasound endoscope according to claim 1, wherein the balloon groove includes a proximal wall forming a proximal end side of the balloon groove, wherein a fourth radial distance from the insertion axis to an outer circumference of the proximal wall is larger than the second radial distance.

6. The ultrasound endoscope according to claim 5, wherein the fourth radial distance is equal to or larger than the first radial distance.

7. The ultrasound endoscope according to claim 5, wherein:
the balloon groove comprises a first balloon groove;
the balloon band comprises a first balloon band;
the end portion of the balloon comprising a distal end of the balloon;
the contact portion comprising a first contact portion;
the distal wall comprising a first distal wall;
the proximal wall comprising a first proximal wall; and
the surface comprising a first surface;
the ultrasound endoscope further comprising:
 a second balloon groove provided on a proximal end side of the ultrasound transducer, the second balloon grove being configured to fit a second balloon band provided at a proximal end portion of the balloon;
 a second contact portion forming a bottom surface of the second balloon groove in contact with the second balloon band;
 a second distal wall forming a distal end side of the second balloon groove, the second distal wall including a second notch provided with a second surface, the second notch being partially provided on the outer circumference of the second distal wall relative to the insertion axis of the insertion portion;
 the second notch has a second surface having a fifth radial distance from the insertion axis to the second surface, the fifth radial distance being equal to or larger than a sixth radial distance and smaller than a seventh radial distance;
 wherein the sixth radial distance being from the insertion axis to the second contact portion and the seventh radial distance being equal to a sum of the sixth radial distance and a thickness of the second balloon band, and
 a second proximal wall forming a proximal end side of the second balloon groove, wherein an eighth radial distance from the insertion axis to an outer circumference of the second proximal wall is larger than the sixth radial distance.

8. The ultrasound endoscope according to claim 5, further comprising an acoustic lens configured to cover an outer circumference of the ultrasound transducer, wherein
in a case where, in a straight line group where each straight line is obtained by connecting an arbitrary first point on a front surface of the surface of the notch and an arbitrary second point on a front surface of the proximal wall, each straight line in the straight line group is disposed so as not to intersect the distal wall and the proximal wall except for the first and second points, the straight line group does not intersect the acoustic lens.

9. The ultrasound endoscope according to claim 5, wherein an inclined surface in which the fourth radial distance is decreased toward a distal end side along the extension direction of the insertion portion is formed on the proximal wall facing the notch in a longitudinal cross section of the proximal wall.

10. The ultrasound endoscope according to claim 9, wherein the inclined surface is formed on the entire circumference of the proximal wall.

11. The ultrasound endoscope according to claim 5, wherein, when a sharp tool is inserted from the notch, the proximal wall is located between the sharp tool and the ultrasound transducer.

12. The ultrasound endoscope according to claim 1, wherein portions of an outer circumference of the distal wall other than the surface has a suborbicular, oval, or circular shape.

13. The ultrasound endoscope according to claim 1, wherein the distal wall having a planar truncation to define the notch on the portion of the outer circumference of the distal wall, the planar truncation being offset radially from an insertion axis extending through a center of a cross-section of the insertion portion, the planar truncation defining the surface of the distal wall having the first radial distance from the insertion axis to the surface.

14. An ultrasound endoscope comprising:
 an ultrasound transducer provided at a distal end of an insertion portion configured to be inserted into a subject, the ultrasound transducer being configured to transmit ultrasound into the subject and receive the ultrasound reflected from the subject;
 a balloon groove provided on a proximal end side of the ultrasound transducer, the balloon groove being configured to fit a balloon band, the balloon band being provided at an end portion of a balloon covering an outer surface of the ultrasound transducer; and
 a distal wall forming a distal end side of the balloon groove, the distal wall having a notch;
 the notch is partially provided only on a portion of an outer circumference of the distal wall in a radial direction relative to an insertion axis extending through a center of a cross-section of the insertion portion,
 the notch defining a surface of the outer circumference of the distal wall having a first radial distance from the insertion axis to the surface, the first radial distance being equal to or larger than a second radial distance and smaller than a third radial distance,
 the second radial distance being from the insertion axis to a contact portion that forms a bottom surface of the balloon groove; and
 the third radial distance being a sum of the second radial distance and a thickness of the balloon band.

15. The ultrasound endoscope according to claim 14, wherein the balloon groove includes a proximal wall forming a proximal end side of the balloon groove, wherein a fourth radial distance from the insertion axis to an outer circumference of the proximal wall is larger than the second radial distance.

16. The ultrasound endoscope according to claim 14, wherein portions of an outer circumference of the distal wall other than the surface has a suborbicular, oval, or circular shape.

17. The ultrasound endoscope according to claim 16, wherein the notch includes two notches.

18. The ultrasound endoscope according to claim 14, wherein the distal wall having a planar truncation to define the notch on the portion of the outer circumference of the distal wall, the planar truncation being offset radially from an insertion axis extending through a center of a cross-section of the insertion portion, the planar truncation defining the surface of the distal wall having the first radial distance from the insertion axis to the surface.

* * * * *